United States Patent [19]

Berger et al.

[11] Patent Number: 5,104,811
[45] Date of Patent: Apr. 14, 1992

[54] TEST CARRIER AND METHOD FOR THE ANALYTICAL DETERMINATION OF COMPONENTS OF BODY FLUIDS

[75] Inventors: Dieter Berger, Viernheim; Wolfgang-Reinhold Knappe, Bürstadt; Robert Lorenz, Ludwigshafen, all of Fed. Rep. of Germany; Henry M. Grage, Jr., Carmel; Mark T. Skarstedt, Indianapolis, both of Ind.; Bernward Sojka, Viernheim; Manfred Bleisteiner, Mannheim, both of Fed. Rep. of Germany

[73] Assignee: Boehringer Mannheim GmbH, Mannheim, Fed. Rep. of Germany

[21] Appl. No.: 134,950

[22] Filed: Dec. 18, 1987

[30] Foreign Application Priority Data

Dec. 19, 1986 [DE] Fed. Rep. of Germany ....... 3643516

[51] Int. Cl.⁵ .................... B01N 21/78; B01N 21/88
[52] U.S. Cl. ..................... 436/164; 422/56; 422/57; 422/58; 427/2; 435/805; 435/810; 436/514; 436/810
[58] Field of Search .......... 422/56, 57, 58; 427/2; 436/514, 810, 164; 435/805, 810

[56] References Cited

U.S. PATENT DOCUMENTS

| | | | |
|---|---|---|---|
| 4,160,008 | 7/1979 | Fenocketti et al. | 422/56 |
| 4,582,684 | 4/1986 | Vogel et al. | 422/58 |
| 4,780,280 | 10/1988 | Berger et al. | 422/56 |
| 4,820,489 | 4/1989 | Rothe et al. | 422/56 |
| 4,857,453 | 8/1989 | Ullman et al. | 422/56 |
| 4,861,711 | 8/1989 | Friesen et al. | 436/7 |
| 4,883,764 | 12/1989 | Kloepfer | 422/56 |

Primary Examiner—David L. Lacey
Assistant Examiner—David Redding
Attorney, Agent, or Firm—Felfe & Lynch

[57] ABSTRACT

On a carrier layer there are arranged several test layers which are at least partly in fluid contact with one another, enabling liquid exchange. On the carrier layer are arranged an application zone, a detection zone for the production of a detectable signal characteristic of the analytical determination, which contains at least one said test layer which is a reaction layer, and an absorption zone with a test layer which is an absorptive layer of an absorbent material, wherein the reaction layer and absorption zone are positioned next to each other. Between the application and the absorption zone is a capillary-active transport path on the carrier layer which connects the application zone and the absorption zone. The reaction layer is arranged parallel to the transport path between the application zone and the absorption zone in such a manner that it is in liquid contact with a liquid transported in the transport path. The absorption zone therefore absorbs excess liquid and permits dosing the reaction layer with a reproducible amount of sample.

11 Claims, 2 Drawing Sheets

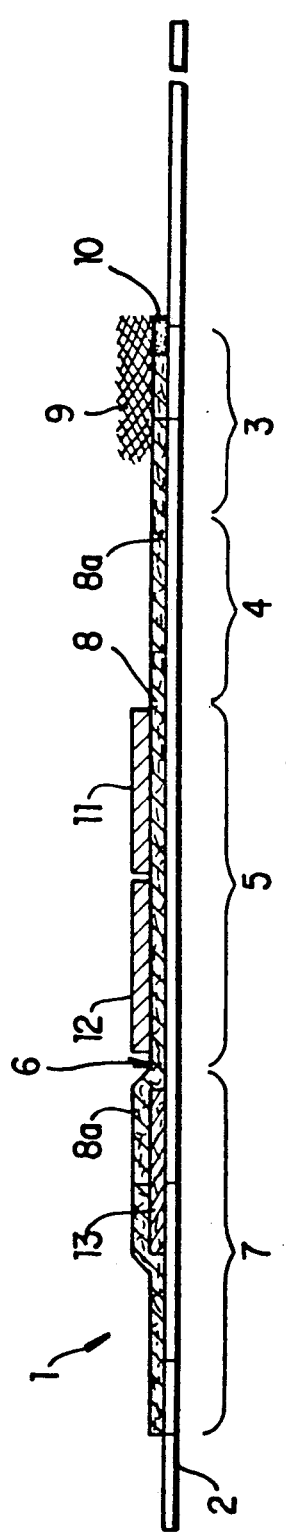
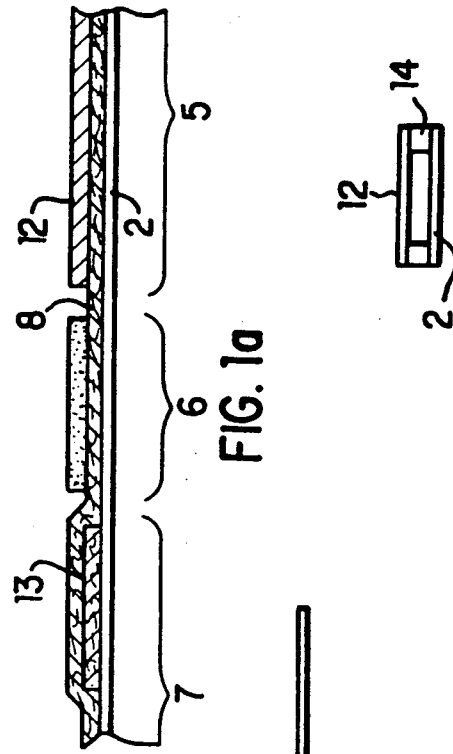
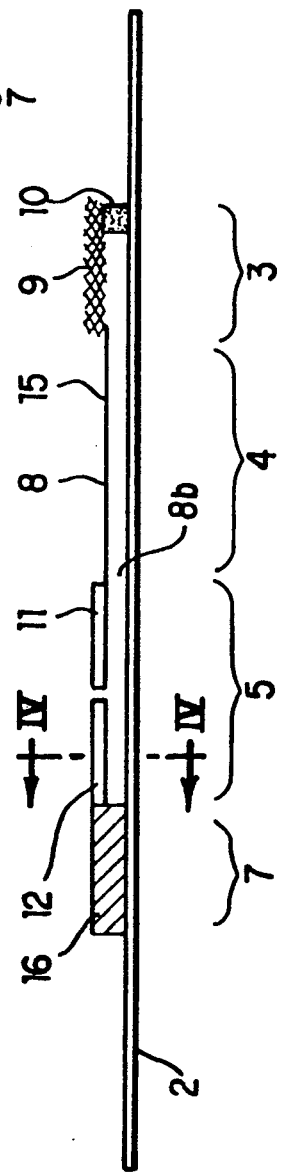
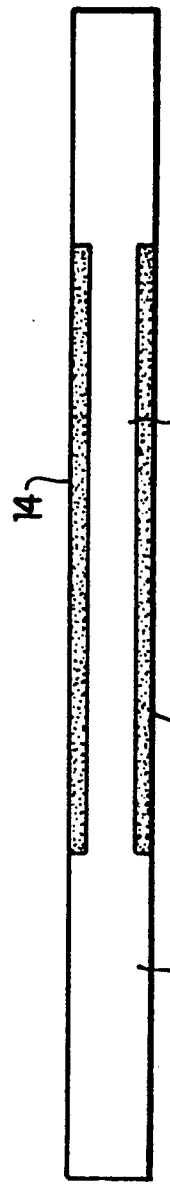

TEST CARRIER AND METHOD FOR THE ANALYTICAL DETERMINATION OF COMPONENTS OF BODY FLUIDS

BACKGROUND OF THE INVENTION

The invention concerns a test carrier for the analytical determination of components of body fluids from an amount of sample. The test carrier contains a carrier layer and several test layers arranged thereupon in such a manner that an exchange of fluid is possible between them. The layers incorporate an application zone for the application of a sample of the body fluid, a detection zone containing at least one detection layer for the production of a detectable signal characteristic for the analytical determination and an absorption zone of an absorbent material arranged in sequence substantially next to one another on the carrier layer.

For the qualitative and quantitative analytical determination of components of body fluids, especially of blood, in recent times so-called carrier bound tests are increasingly employed. In these, reagents are embedded in layers of a solid test carrier which is brought into contact with the sample. The reaction of sample and reagents leads to a detectable signal, especially a color change, which can be evaluated visually or with the help of an apparatus, usually a reflection-photometer.

Test carriers are frequently constructed as test strips which consist essentially of a longitudinal carrier layer of synthetic resin material and test fields applied thereto. However, test carriers are also known which are formed as quadratic or rectangular platelets.

Carrier-bound tests are characterized especially by the simplicity of their handling. The result of this is that such tests are also being used more and more by lay persons or for use in at home diagnosis where specialized laboratory personnel are not always available.

Previously known test carriers work without sample dosing, and reproducible impregnation of the reaction layer of the test carrier is achieved by first applying the sample in excess and the sample excess is then wiped off or washed off. Handling of the test carrier is thereby made difficult. In particular, however, wiping off or washing off leads to user-dependent sources of error if it is not carried out completely correctly.

From German Patent Specification No. 34 45 816, a strip-shaped test carrier is known in which, on a carrier layer, several absorbent test layers are present arranged next to one another in such a, manner that they are in absorbent contact with one another via their edges. This known test carrier is intended for immunological tests in which, apart from the sample, an elution agent is employed. The elution agent is applied to one end of the overall longitudinal test carrier and migrates through the test layers in the form of a liquid stream which comes to a stop at the other end of the test carrier. The sample is applied either at the same place as the elution agent or in the middle region of the carrier. This patent application does not address the problem of the dosing of the sample in a reaction layer of the test carrier. Dosing plays no part in the use of the carrier because the sample is introduced in precise dosaging into the elution agent stream and the elution agent is introduced until it completely fills the test carrier.

SUMMARY OF THE INVENTION

It is an object of the present invention to provide a test carrier comprising a reaction layer reproducably impregnated with at least one reagent and which does not require wiping off or washing off of the excess sample. This is to be accomplished with the smallest possible expense and also with small amounts of sample, for example a blood droplet obtained from a prick in the finger tip.

The carrier layer is preferably formed longitudinally as in the case of a conventional test strip and preferably consists of a synthetic resin foil.

On this are positioned next to one another an application zone, a detection zone and an absorption zone. The application zone serves to conduct the sample to the test carrier. The application zone is connected with the absorption zone by a capillary action transport path.

The term "capillary-active transport path" is, in particular, to be understood to be a means connecting the application zone and the absorption zone for liquid transport from the sample application zone to the absorption zone, whereby the liquid transport depends upon capillary action. Of special importance for the capillary action are the surface properties of the participating materials and the distances of the solid surfaces in the transport layer. In order to achieve good transport action, a material is chosen which is well wetted by the sample fluid, possibly with the help of suitable wetting agents. Furthermore, it is desirable that the layer consists of a structure with solid surfaces lying close to one another for a good capillary action. In particular, they may consist, for example, of a fibrous structure (e.g. fleece or fabric). Other open and porous structures which make possible a liquid transport in the longitudinal direction of the layer can also be used, however. Especially preferred is an apparatus where the transport path contains one or more slits running from the sample application zone to the absorption zone.

The absorption zone contains at least one absorbent layer of an absorbent material. An absorbent material in this sense is any material which is able to take up liquid. Uptake of liquid can take place with the help of the capillary action described in connection with the transport path. There are, however, also other possibilities. For example, uptake of water by hydration, and swelling or volume expansion of the absorbent layer.

The detection zone is the region of the test carrier in which, after carrying out of the analysis, the detectable signal can be measured. It contains one or more reaction layers in which reagents are present, the reaction of which with the sample finally leads to the detectable signal. Most desirably this signal is a visually or photometrically evaluable color change.

An important feature of the invention is to be seen in the fact that a reaction layer is arranged within the detection zone, parallel to the transport path, in such a manner that it stands in fluid contact with a liquid transported in the transport path. In the commonest form of the invention, it is not necessary that the reaction layer is immediately neighboring the transport path. Intermediate layers can also be present which permit a liquid transport from the transport path to the reaction layer. The reaction layer can be arranged between the carrier layer and the transport path or on the side of the transport path facing away from the carrier layer.

The invention is directed in particular to tests wherein it is important that, independently of the amount of sample, the amount of the liquid taken up by the reaction layer is reproducably substantially equal. In this regard, it is especially advantageous when the absorbent zone, the transport path and the reaction layer are appropriately attuned to one another with regard to their absorption power, speed of absorption and absorption volume. It is the object of these measures that the liquid in the transport path is available at least until the reaction layer has taken up a reproducable amount of liquid. Thereafter, the liquid connection between the transport path and the reaction layer is to be broken off. Further detail are set forth infra.

BRIEF DESCRIPTION OF THE DRAWINGS

FIG. 1 shows a test carrier according to the invention in longitudinal section;

FIG. 1A ia a partial longitudinal cross section of the test carrier of FIG. 1 with the addition of a sample recognition zone;

FIG. 2 shows another embodiment of a test carrier according to the invention in longitudinal section;

FIG. 3 shows a top view of the carrier layer of a test carrier according to FIG. 2 in a not yet finally assembled state;

FIG. 4 shows a cross-section through a test carrier according to FIG. 2 along the line IV—IV.

DETAILED DESCRIPTION OF THE PREFERRED EMBODIMENT

Figure 5:
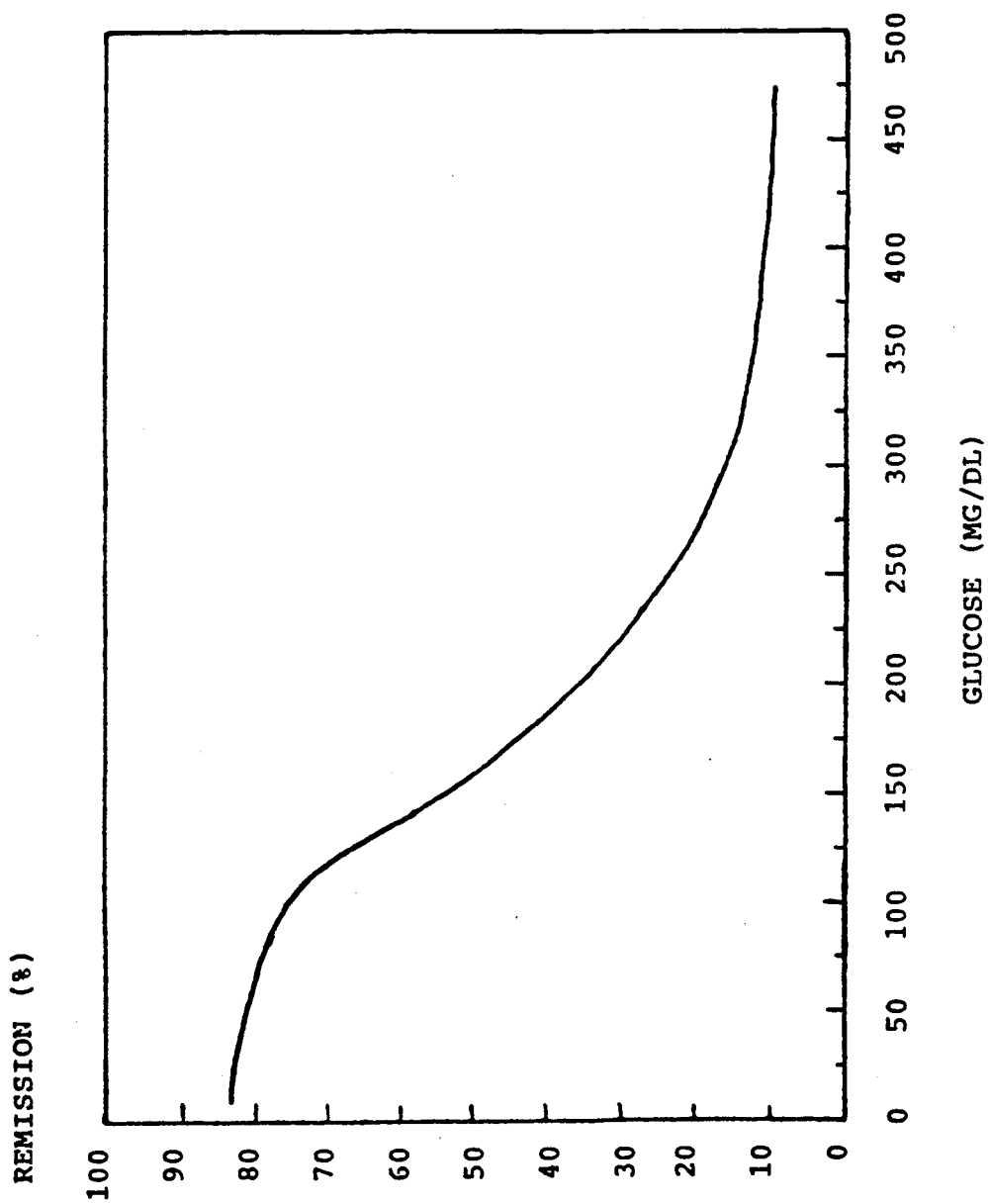
FIG. 5 shows a function curve for the relationship between % remission of a reaction layer of a test carrier according to the invention and the amount of glucose in a sample to be investigated.

The test carrier 1 illustrated in FIG. 1 consists essentially of a carrier layer 2 and test layers arranged thereon. The carrier layer 2 is formed longitudinally. It is preferably approximately 100 mm. long, about 5-6 ;mm. wide and 0.3-0.4 mm. thick.

The test carrier can be divided up in its longitudinal direction into an application zone 3, a transport zone 4, a detection zone 5 and an absorption zone 7.

In the case of the embodiment illustrated in FIG. 1, the capillary action transport path 8 is formed by a transport layer 8a of a fibrous material (e.g. fleece or fabric) extending from the beginning of the application zone 3 up to the end of the absorption zone 7. It suffices when the transport path 8 connects the application zone 3 and the absorption zone 7. Polyamide has proved to be an especially suitable material for a transport path constructed in the form of a fabric or fleece.

The transport layer 8a and the protective net 9 present thereover in the application zone are jointly connected with a melt adhesive strip 10 to the carrier layer 2.

In the region of the detection zone 5, parallel to the transport path 8, the reaction layers 11 and 12 are applied parallel and immediately neighboring to this. They can be fixed, for example, on the transport layer 8a or on the carrier layer 2. Although in each case two reaction layers are illustrated, the invention can, of course, also be carried out with only one reaction layer or with more than two reaction layers. Each of the reaction layers 11, 12 can also, in turn, consist of a multilayer construction which, for the purpose of this invention, is regarded as a unit.

In the region of the absorption zone 7, parallel to the transport layer between this and the carrier layer 2, there is present an absorbent layer 13 which preferably consists of a material which, on the basis of its good wettability, has a high absorptive power. A fleece or fabric of glass fibers has proved to be especially suitable.

In the case of the test carrier illustrated in FIG. 2, the capillary action transport path 8 is made in the form of a canal-shaped slot 8b. As, is to be seen from FIG. 3, the slot 8b is bound by two narrow strips 14 of transfer adhesive band which are stuck along on the carrier layer 2. In the upward direction, the canal-shaped slot is covered by a covering foil 15 or by the reaction layers 11 and 12. In the case of the embodiment illustrated in FIGS. 2-4, the absorption zone 7 consists essentially of a single block-shaped absorption layer 16.

To carry out an analytical determination, a small amount of sample is applied to the application zone 3, for example, a droplet of blood of about 15 $\mu$l. volume, such as can easily be obtained from the finger tip is sufficient. The sample passes through the protective mesh 9 into the application zone 3 and via the transport zone 4, on the basis of the capillary activity of the transport path 8, into the detection zone 5 and further into the absorption zone 7. To be able to determine whether the sample volume applied to the application zone is sufficient to carry out an analytical determination there may be arranged a sample recognition zone 6 between detection zone 5 and absorption zone 7, which, when being contacted by the sample liquid, shows in a detectable manner, that a sufficient amount of sample has been applied to the test carrier (FIG. 1A). In the passage through the detection zone 5, a liquid contact with the reaction layers 11 and 12 occurs so that these absorb fully. As mentioned above, the absorption power, the absorption speed and the absorption volume of the reaction layers 11, 12, of the transport path 8 and of the absorption zone 7 (which is essentially determined by the properties of the absorption layer 13, 16) are so attuned to one another that the liquid in the detection zone 5 is available at least until the reaction layers 11 and 12 have taken up a definite amount of liquid. Thereafter the liquid is further absorbed by the absorption zone 7 at least to such an extent that the liquid contact between the reaction layers 11, 12 and the transport path is interrupted.

The speed of the transport of the sample liquid in the capillary action transport path 8 is determined, on the one hand, by capillary force and, on the other hand, by flow resistance. The narrower the capillaries in the transport path 8, the higher the capillary force but also, the higher the flow resistance. In the case of a test carrier with a canal-shaped transport path according to FIG. 2, a canal slot, with a width of 0.3 mm., fills in 4 seconds, while a slot width of 0.2 mm, fills in about 6 seconds, and a slot width of about 0.1 mm. in 30 seconds. In the case of a slot width of 0.05 mm the filling time of the canal is more than 30 seconds. One sees that, in this range, the influence of increasing flow resistance preponderates with respect to the increasing capillary force and, therefore, the speed of flow increases as the capillary size becomes smaller.

The speed of absorption with which the reaction layers 11, 12 fill is dependent upon their properties. Depending upon the use contemplated, very different reaction layers are used in the test carriers. For example, the reagents can be impregnated on a paper, fleece or on a matrix of a porous synthetic resin material. Reaction layers are also used with a swellable carrier material, for example a gel or a gelatine layer. The speed of absorption with which the reaction layers absorb fully can, in each case, be determined empirically by the skilled artisan. With respect to the invention, the sample liquid in the capillary action path 8 is to be available at least until the reaction layers 11, 12 have absorbed the liquid to the desired extent. When this takes place is, in particular, dependent upon the speed with which the absorption zone takes up the sample liquid and upon the amount of sample. If one proceeds from a particular maximum amount of sample which can be investigated with the test carrier, then it is preferred that the total amount of liquid which the test carrier can take up (the "absorption volume" of the test carrier, which consists essentially of the liquid take up of the transport path 8, of the reaction layers 11, 12 and of the absorption zone 7) is greater than the maximum amount of sample.

Preferably the absorption volume of the absorption layer is greater than the amount of sample to be analyzed. An especially preferred test carrier according to the invention comprises an absorption zone with an absorption volume which is greater than the absorption volume of the transport path.

The absorption zone 7 preferably takes up the liquid at a rate considerably slower than the transport path. The liquid flow thereby slows down very considerably as soon as the liquid front has reached the beginning of the absorption zone 7. The further flow through the transport path 8 is then determined by the speed of absorption of the absorption zone, i.e. how quickly the absorption zone takes up the liquid. This procedure is to be so slow that the reaction layers 11, 12 have sufficient time to fill with sample liquid.

When, finally, the amount of sample applied to the application zone 3 is consumed but the absorption zone has not yet taken up its maximum absorption volume, the absorption zone 7 begins to suck empty the capillary action transport path 8. For this purpose, it is necessary that the absorptive power of the absorption zone 7 is greater than that of the capillary-active transport path 8. This can be achieved, for example, in that the absorptive layer 13, 16 contained in the absorption zone 7 consists of a capillary action material with especially high wettability for the sample liquid, for example of glass fibers.

In the case of the emptying of the capillary action transport path 8, the liquid contact with the reaction layers 11, 12 is to be interrupted without losing liquid to a noteworthy extent, which would impair the precision. Therefore, it is preferred that the reaction layers 11, 12 have a higher absorptive power than the capillary action transport path 8.

The additional transport zone 4 between application zone 3 and detection zone 5 can be expedient when a test carrier is desired in which the application zone 3 and the detection zone 5 do not lie very close to one another.

Example 1

Test carrier for the measurement of glucose

The test carrier is constructed according to FIGS. 2, 3 and 4:

The carrier layer 2 consists of a polyester film (thickness 0.5 mm., length 77 mm., breadth 6 mm.). On this are fixed protective net 9, a covering film 15 and the reaction layers 11 and 12 with two transfer adhesive strips 14 (double sided adhesive strip)(thickness 0.1 mm., length 43 mm., breadth 1.5 mm.) arranged in parallel.

The protective net 9 is a polyester net (PE 280 HC, Schweizer Seidengazefabrik Thal, Switzerland), mesh width 280 μm., thickness 0.2 mm., length 8 mm., breadth 6 mm. On one side, it is fixed with a melt adhesive strip 10 on to the polyester film 2. The covering film 15 is a polyester film coated on one side with agarose (Gel-Fix, Serva, Heidelberg, Federal Republic of Germany) (thickness 0.18 mm., length 10 mm., breadth 6 mm.), the coated side of which faces the carrier layer 2.

The reaction layers 11 and 12 are produced as follows:

198 g. acrylic acid ester co-polymer dispersion (Acronal 14D of BASF, Ludwigshafen, Federal Republic of Germany; 55% in water)

174 g. swollen, highly viscous methylhydroxyethylcellulose (0.5% in water)

336 g. kieselguhr 336 g. titanium dioxide 0.95 g. tetraethylammonium perfluorooctane-sulphonate 40 g. 0.5M phosphate buffer (pH 5.5)

23 g. methanol 46 g. hexan-1-0l 69 g. acetone 65 g. water are worked up to give a homogeneous first coating mass and coated with a 0.18 mm. slot height on to a 0.20 mm. thick polyester filter fabric (2 F 777, Schweizer, Seidengazefabrik Thal, Switzerland) and dried.

On to the coated carrier thus obtained is applied a second coating mass consisting of 102 g. acrylic acid ester co-polymer dispersion (Acronal 14D of BASF, Ludwigshafen, Federal Republic of Germany, 55% in water)

38 g. swollen, highly viscous methylhydroxyethylcellulose (0.5% in water) 3 g. sodium dodecylbenzenesulphonate 36 KU glucose oxidase 1050 KU peroxidase 1.48 g. 3, 3',5, 5'-tetramethylbenzidine 0.53 g. 1-phenylsemicarbazide 28 g. 1-methoxypropan-2-ol 40 g hexan-1-ol 38 g water which have been worked up to give a homogeneous mass, with a 0.02 mm. slot height and dried.

The two reaction layers 11 and 12 used each have a length of 6 mm. and a breadth of 6 mm. They are so fixed next to one another that there is no gap between them.

The absorption layer 16 consists of a glass fiber fleece with a weight per unit surface area of 60 mg/m$^2$ (thickness 0.3 mm., length 12 mm., breadth 6 mm.).

For the measurement of glucose, 20/μl. of blood are applied to the application zone 3 of the test carrier. After 2 minutes at ambient temperature, the reaction layers 11 and 12 are measured reflection photometrically at a wavelength of 660 nm.

A function curve (FIG. 5) was produced with samples of known glucose concentration in which a measurement value in remission is plotted against a known glucose concentration. Samples with unknown glucose content can also be measured quantitatively with the help of such a curve.

It will be understood that the specification and examples are illustrative but not limitative of the present invention and that other embodiments within the spirit and scope of the invention will suggest themselves to those skilled in the art.

We claim: We claim:

1. Test carrier for determination of a component of a fluid sample, said carrier comprising a carrier layer and being divided longitudinally into a plurality of zones, said zones comprising:
   (a) an application zone on said carrier layer for application of said fluid sample, said application zone comprising means for receiving said fluid sample;
   (b) a detection zone on said carrier layer, said detection zone containing a reaction layer which comprises means for producing a detectable signal indicating the presence of said component;
   (c) an absorption zone on said carrier layer and containing an absorptive layer, wherein said absorption zone and detection zone are positioned next to each other on said carrier layer said absorptive layer comprising material having absorptive power, said reaction layer comprising material having absorptive power greater than the absorptive power of the material of said absorptive layer; and
   (d) capillary action transport means connecting said application zone and said absorption zone in flow communication said transport means and reaction layer positioned parallel to and in liquid contact with each other at a point between said application zone and said absorption zone so as to permit contact with said fluid sample by both said transport means and said reaction layer.

2. Test carrier of claim 1, wherein said capillary action transport means comprises material having absorptive power and said absorption zone comprises material having an absorptive power greater than the absorption power of said material in said transport means.

3. Test carrier of claim 1, wherein said capillary action transport means comprises material having absorptive power and said reaction layer comprises material having absorptive power greater than the absorptive power of said material in said capillary action transport means.

4. Test carrier of claim 1, further comprising a liquid transport zone arranged on said carrier layer positioned between said application zone and said detection zone and in flow communication with said application and said detection zone, said capillary action transport, meons extending from said application zone through said transport zone to said detection zone.

5. Test carrier of claim 1, wherein said capillary active transport meons comprises a transport layer of fibrous material.

6. Test carrier of claim 1, wherein said capillary action transport meons comprises a slot of at least 0.05 mm width.

7. Test carrier of claim 1 further comprising a sample recognition zone positioned between said detection zone and said absorption zone and in flow communication with said detection zone and said absorption zone, which recognition zone comprises means for showing in a detectable manner that a sufficient amount of sample has been applied at said application zone.

8. The test carrier of claim 1, wherein said absorptive layer of said absorption zone and said transport means comprise materials having an absorption volume, the absorption volume of said absorptive zone being greater than the absorption volume of said transport means.

9. Test carrier of claim 6, wherein said slot is from about 0.15 to about 0.20 mm in width.

10. Method for determining a component of a fluid sample, comprising:
    contacting said fluid sample with a test carrier, said test carrier comprising a carrier layer, and being divided longitudinally into a plurality of zones including an application zone on said carrier layer for application of said fluid sample, said application zone comprising means for receiving said fluid sample; a detection zone on said carrier layer and containing a reaction layer which comprises means for producing a detectable signal indicating the presence of said component, said reaction layer comprising material having absorptive power, an absorption zone on said carrier layer and containing an absorptive layer comprising material having absorptive power, said absorptive power of said material of said reaction layer being greater than the absorptive power of the material of said absorptive layer, wherein said absorption zone and detection zone are positioned next to each other on said carrier, and a capillary action transport means on said carrier layer and connecting said application and absorption zones in flow communication with said transport means and reaction layer being positioned parallel to each other at a point between said application and absorption zones, wherein said contacting of said fluid with said test carrier permits contact of said fluid with both said transport means and reaction layer, and
    (b) determining production of a detectable signal in said reaction layer as a determination of said component.

11. Method for determining a component sample as in claim 10 wherein said test carrier further comprises a sample recognition zone positioned between said detection zone and said absorption zone and in flow communication with said detection zone and absorption zone, said method comprising the additional step of determining that sufficient sample has been applied to said test carrier by measurement at the sample recognition zone.

* * * * *